United States Patent [19]

Linstid, III et al.

[11] Patent Number: 4,537,995
[45] Date of Patent: Aug. 27, 1985

[54] ISOMERIZATION OF BRANCHED ALDEHYDES TO KETONES

[75] Inventors: H. Clay Linstid, III, Maplewood; Gerald S. Koermer, Springfield, both of N.J.

[73] Assignee: Celanese Corporation, New York, N.Y.

[21] Appl. No.: 549,129

[22] Filed: Nov. 7, 1983

[51] Int. Cl.³ ............................................. C07C 45/67
[52] U.S. Cl. .................................... 568/384; 568/310; 568/341
[58] Field of Search ....................... 568/384, 341, 310; 585/481; 502/77

[56] References Cited

U.S. PATENT DOCUMENTS

| 4,011,278 | 3/1977 | Plank et al. | 568/388 |
| 4,159,282 | 6/1979 | Olson et al. | 585/481 |
| 4,188,282 | 2/1980 | Tabak et al. | 585/481 |
| 4,329,506 | 5/1982 | Velenyi et al. | 568/384 |
| 4,427,790 | 1/1984 | Miale et al. | 502/77 |

OTHER PUBLICATIONS

Lange et al., Neftekim, vol. 16, #6, pp. 818-822 (1976).

Primary Examiner—James H. Reamer
Attorney, Agent, or Firm—Charles B. Barris

[57] ABSTRACT

A process of isomerizing branched aldehydes to ketones is provided which comprises contacting at isomerization conditions a branched aldehyde with a zeolite catalyst of the formula:

$$(0.9 \pm 0.2) \frac{M_2O}{n} : Al_2O_3 : xSiO_2 \qquad (I)$$

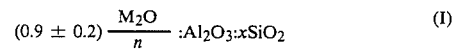

wherein M is selected from the group consisting of a mixture of alkali metal cations, especially sodium, and tetraalkylammonium cations, the alkyl groups of which preferably contain 2 to 5 carbon atoms, and x is at least 5. The contacting is conducted at a temperature of from about 200° C. to about 600° C. and at a pressure of from about 20 psig to about 100 psig. The branched aldehyde is contacted in the presence of water in a molar ratio of water-to-aldehyde of up to about 20 to 1.

6 Claims, No Drawings

ISOMERIZATION OF BRANCHED ALDEHYDES TO KETONES

BACKGROUND OF THE INVENTION (1) Field of the Invention

This invention relates to the isomerization of aldehydes, such as isobutyraldehyde, to ketones, such as methyl ethyl ketone (MEK).

(2) Description of the Prior Art

Canter et al, U.S. Pat. No. 3,384,668, teach the isomerization of aliphatic aldehydes to ketones by contacting a vaporous aldehyde with a solid acidic catalyst, e.g., phosphoric acid on a support, at a temperature above 100° C.

Hargis et al, U.S. Pat. No. 3,453,331, teach the production of symmetrical and unsymmetrical ketones from aldehydes by contacting an aldehyde with an oxidized form of a rare earth metal having an atomic number of 59 to 71 supported on an activated alumina. The process is a vapor-phase process.

Velenyi et al, U.S. Pat. No. 4,329,506, teach that aldehydes, such as isobutyraldehyde, are isomerized to ketones, such as methyl ethyl ketone, by contact at isomerization conditions, typically vapor-phase conditions, with a catalyst of the formula $M_{0.15-15}M'_{0.05-12}O_x$ where M is at least one of Mo and Cu and M' is a promoter, such as a Group IIB or VIII element.

S. A. Lange et al, "Isomerization of Isobutyraldehyde to Methyl Ethyl Ketone", Neftekhim. 16, No. 6, 818–822 (1976) [Russian] teach the skeletal isomerization of isobutyraldehye to methyl ethyl ketone in the presence of zeolite-containing aluminosilicate catalysts, HY Zeolites, in a stream of steam. They report that the selectivity of MEK formation passes through a maximum at a temperature of from 450° to 470° C. and that the presence of water in the raw material feed significantly enhances the yield of MEK.

SUMMARY OF THE INVENTION

According to this invention, aldehydes, especially branched aldehydes, such as isobutyraldehyde, are isomerized to ketones, such as methyl ethyl ketone (MEK), by a process comprising contacting at isomerization conditions an aldehyde with a catalyst composition comprising a crystalline aluminosilicate zeolite characterized by a silica/alumina mole ratio of greater than 12 and a constraint index of from about 1 to about 12.

The crystalline aluminosilicate zeolites used in the catalyst composition of the process of this invention are referred to generally as ZSM-5 type or as behaving like ZSM-5 and are represented by the general formulas, expressed in terms of mole ratios of oxides in the anhydrous state, as follows:

$$(0.9 \pm 0.2) \frac{M_2O}{n} : Al_2O_3 : xSiO_2 \qquad (I)$$

wherein M is a cation, predominately non-noble metal of Group VII of the Periodic Table and/or hydrogen, n is the valence of M and X is at least 5.

The process is typically conducted in the vapor phase utilizing relatively low temperatures, e.g., temperatures as low as 325° C. and lower, and less water cofeed than heretofore reported in the prior art, e.g., a water-to-isobutyraldehyde molar ratio as low as about 0.03.

DETAILED DESCRIPTION OF THE INVENTION

Any branched aldehyde that can be isomerized to a ketone could be used in the practice of this invention. Typical aldehydes are of the formula

where R, R' and R" are hydrogen, aliphatic, alicyclic, aryl or an inertly-substituted aliphatic, alicyclic or aryl radical with the proviso that all are not simultaneously hydrogen, aryl or inertly-substituted aryl. Preferably R, R' and R" are independently hydrogen, $C_1$–$C_4$ alkyl or phenyl. Preferably the aldehyde contains but a single aromatic group, i.e., only one of R, R' and R" is phenyl. "Inertly-substituted" and like terms here mean that the R, R' and R" substituents can bear functional groups, e.g., alkoxys, halogen, etc., that are essentially nonreactive with the starting materials, catalysts and products of the process at process conditions. Isobutyraldehyde is particularly adapted for conversion to its isomeric ketone, methyl ethyl ketone, in high conversion and yield by the procedure of this invention.

While isobutyraldehyde is preferred, the invention extends to the use of the other di- and trialkyl-substituted branched aldehydes as starting materials. Suitable aldehyde feeds include, in addition to isobutyraldehyde, 2-methylbutyraldehyde, 2-methylpentaldehyde, 2-ethylhexaldehyde, and 2,2-dimethylpropionaldehyde.

The ketones produced by this invention are the isomerized products of a starting aldehyde. Aldehydes of formula (II) produce ketones of the formula

where R, R' and R" are as defined in formula (II).

The catalyst composition useful in this invention comprises a crystalline aluminosilicate zeolite characterized by a silicon/aluminum mole ratio of at least 12 and a constraint index of from about 1 to about 12.

Zeolite ZSM-5 is taught by U.S. Pat. No. 3,702,886, issued Nov. 14, 1972, the disclosure of which is incorporated herein by reference. In a preferred synthesized form, the zeolite ZSM-5 for use in the catalyst composition useful in this invention has a formula, in terms of mole ratios of oxides in anhydrous state, as follows:

$$(0.9 \pm 0.2) \frac{M_2O}{n} : Al_2O_3 : xSiO_2 \qquad (I)$$

wherein M is selected from the group consisting of a mixture of alkali metal cations, especially sodium, and tetraalkylammonium cations, the alkyl groups of which preferably contain 2 to 5 carbon atoms, and x is at least 5. Particularly preferred is a zeolite having the formula in the anhydrous state as follows:

$$(0.9 \pm 0.2) \frac{M_2O}{n} : Al_2O_3 : ZSiO_2 \qquad (IV)$$

wherein Z is from greater than 30 to about 350 or higher.

The original cations can be replaced in accordance with techniques well-known in the art, at least in part, by ion exchange with other cations. Preferred replacing cations include tetraalkylammonium cations, metal ions, ammonium ions, hydrogen ions and mixtures of the same. Particularly preferred cations are those which render the zeolite catalytically active, especially for hydrocarbon conversion. These include hydrogen, rare earth metals, aluminum, metals of Groups II and VIII of the Periodic Table and manganese.

Isomerization conditions are used in the practice of this invention and these will vary with the aldehydes, catalysts, reactor, etc. employed. This process is a heterogeneous catalytic process, i.e., the catalyst is in the solid state while the aldehyde is either in the gaseous or liquid state. Preferably, the aldehyde is in the gaseous state when contacted with the catalyst.

Any temperature at which the aldehyde is either a liquid or gas can be employed with a typical minimum temperature being about 200° C. Economy, convenience and degradation of aldehyde, ketone and catalyst are the principal constraints upon the maximum temperature employed and a typical maximum temperature is about 800° C. The present invention, however, allows for the use of lower temperatures than typical isomerization reactions. The range utilized herein is from about 200° to 600° C., preferably 300° to 400° C. Pressures ranging from subatmospheric to superatmospheric can be used. More typically, pressures in the range of about 20 psig to about 100 psig are used.

If the aldehyde is in the gaseous state at the reaction temperature, then it can be used by either itself or diluted with a relatively inert sweep gas, such as nitrogen, argon, helium, carbon dioxide, steam and the like. Steam is the preferred diluent. Likewise, if the aldehyde is a liquid at the reaction temperature, then it also can be used either alone or with a suitable diluent. Representative diluents include water, mixed hexanes and heptanes, cyclohexane, benzene, etc. with water being preferred.

It has been found that the presence of water in the raw material feed strongly affects the yield of MEK produced. Water is also a principal liquid by-product during conversion of isobutyraldehyde. The molar ratio of water to aldehyde can range as high as 20 and above. However, the process of the present invention, advantageously, has high conversions of aldehyde with concomitant high selectivity to ketones with molar ratios of water to aldehyde as low as 0.03. This represents a technical advance because the greater amount of water needed to be separated, the greater amount of energy is expended. Thus, the amount of diluent utilized can range from about 0.03 mole up to about 20 mole of diluent per mole of aldehyde and, preferably, ranges from about 0.05 to 15 mole of diluent per mole of aldehyde feed.

Contact or residence time can also vary widely, depending upon such variables as the aldehyde, catalyst, reactor, temperature and pressure. Typical contact times range from a fraction of a second to more than several hours with preferred contact times, at least for gaseous phase reactions, between about 0.1 and 10 seconds with contact times in the range of 0.5 to 5 seconds being preferred.

Typically, the catalyst is employed in a fixed bed reactor where the reactant, typically in the gaseous form, is passed over or through the catalyst. Other reactors, such as fluid or ebullient bed reactors, can be employed, if desired.

The following examples are illustrative embodiments of this invention. Per pass conversion (PPC) is calculated by dividing the moles of total product times 100 by the moles of aldehyde fed. The selectivity was calculated by dividing the PPC to the ketone by the PPC of the total product.

SPECIFIC EMBODIMENTS

Catalyst Preparation

Zeolite ZSM-5, for use in the process of this invention, was prepared as indicated in U.S. Pat. No. 3,702,886, incorporated herein by reference above. In a mortar, a small amount, i.e., 0.001 gram of ZSM-5 catalyst (in the proton form) was mixed into about 1 gram of quartz wool fibers. About 0.1 cc of this "loaded" quartz wool was then placed into a pulse reactor mounted in the injection port of a gas chromatograph.

HY Zeolite, for use for comparative purposes, was prepared by treating ammonium Y Zeolite at 350° C. in air for 2 hours. It was prepared for use herein as set out above.

EXAMPLE 1

A series of runs was carried out comparing the vapor phase contact of isobutyraldehyde with fixed bed ZSM-5 and HY Zeolite catalysts. The runs were carried out utilizing a pulsed feed. Water and isobutyraldehyde were fed by syringe and were vaporized in the injection port of the gas chromatograph. The vapors were passed downwardly through a tubular reactor having in its lower portion the ZSM-5 catalyst as prepared above or any HY catalyst being in the form of the catalyst bed was maintained at the reaction temperature of 375° C. The products were passed directly onto a column for analysis.

EXAMPLE 1

| Run No. | Temp., °C. | Contact time, (seconds) | Molar ratio $H_2O/IBH$ | Injection Size (microliters) | Conversion of IBH HY | Conversion of IBH ZSM-5 | Selectivity to MEK HY | Selectivity to MEK ZSM-5 |
|---|---|---|---|---|---|---|---|---|
| 1 | 375 | 0.1 | 11 | 1 | 87 | 81 | ND | 17 |
| 2 | 375 | 0.1 | 11 | 3 | * | 71 | * | 18 |
| 3 | 375 | 0.1 | 11 | 5 | 65 | 45 | ND | 36 |
| 4 | 375 | 0.1 | 0.05 | 0.1 | 49 | 49 | 2 | 18 |

*no comparative example run for HY

The conclusions which can be reached from this Example are that lower temperatures can be used successfully with the ZSM-5 catalyst of the invention and that selectivities are consistently higher using the ZSM-5 catalyst. An additional conclusion is that at even extremely low Water-to-Isobutyraldehyde ratios (Run No. 4–0.05 H₂O/IBH) an impressive selectivity to MEK is attained with the ZSM-5 as compared with the HY.

EXAMPLE 2

A series of runs was carried out involving the vapor phase contact of isobutyraldehyde with a fixed bed HY Zeolite catalyst. Water and isobutyraldehyde were fed through separate pumps and were then vaporized. The vapors were passed downwardly through a tubular reactor having in its lower portion the HY catalyst in the form of the catalyst described in Example 1; 8 cc's of catalyst were employed. The bed was maintained at the reaction temperature indicated. A condenser, liquid nitrogen-cooled, and trap were used to collect the product.

The amount of MEK yield, which proved to be non-detectable, was determined by gas chromatography analysis of the condensate.

EXAMPLE 2

| Run No. | Temp., °C. | Contact time, seconds | Molar ratio H$_2$O/IHB | Length of run, hrs. | Feed ml/min | MEK Yield |
|---|---|---|---|---|---|---|
| 5 | 330 | 1.0 | 11 | 6 | 0.13 | ND |
| 6 | 410 | 1.0 | 11 | 6 | 0.13 | ND |
| 7 | 550 | 1.0 | 11 | 6 | 0.38 | ND |

ND = non-detected

EXAMPLE 3

A series of runs was carried out involving the vapor phase contact of isobutyraldehyde with a fixed bed ZSM-5 catalyst. The reactor utilized and procedure were similar to those of the preceding Example 2. However, the vapor stream was analyzed on line by gas chromatography prior to condensation on an hourly basis.

EXAMPLE 3

| Run No. | Temp., °C. | Contact time, seconds | Molar ratio H$_2$O/IBH | Length of run at sampling (hours) | Feed ml/min | Conversion of IBH | Selectivity to MEK |
|---|---|---|---|---|---|---|---|
| 8 | 500 | 1.0 | 11 | 1 | 0.2 | 33 | 7 |
|   | 500 | 1.0 | 11 | 2 | 0.2 | 43 | 16 |
|   | 500 | 1.0 | 11 | 3 | 0.2 | 72 | 5 |
|   | 500 | 1.0 | 11 | 4 | 0.2 | 70 | 14 |
| 9 | 500 | 1.0 | 0.04 | 1 | 0.2 | 14 | 63 |
|   | 500 | 1.0 | 0.04 | 2 | 0.2 | 17 | 59 |
|   | 500 | 1.0 | 0.04 | 3 | 0.2 | 30 | 17 |
| 10 | 500 | 1.0 | 0.04 | 1 | 0.2 | 100 | 10 |
|   | 500 | 1.0 | 0.04 | 2 | 0.2 | 67 | 50 |
|   | 500 | 1.0 | 0.04 | 3 | 0.2 | 60 | 25 |
|   | 500 | 1.0 | 0.04 | 4 | 0.2 | 54 | 24 |
|   | 500 | 1.0 | 0.04 | 5 | 0.2 | 50 | 23 |

The benefits accruing from the use of a ZSM-5 catalyst are indicated in the tabular results of Example 3, when compared to those of Example 2.

What is claimed is:

1. A process for isomerizing branched aldehydes to ketones which comprises contacting a 2-alkyl substituted aldehyde with a ZSM-5 type crystalline aluminosilicate zeolite at a temperature from about 200° C. to about 600° C. in the presence of water in a molar ratio range from about 0.03 to about 20 moles of water per mole of aldehyde.

2. A process in accordance with claim 1 wherein the 2-alkyl substituted aldehyde is isobutyraldehyde.

3. A process in accordance with claim 1 wherein the 2-alkyl substituted aldehyde is 2-methylbutyraldehyde.

4. A process in accordance with claim 1 wherein the 2-alkyl substituted aldehyde is 2-methylpentaldehyde.

5. A process in accordance with claim 1 wherein the 2-alkyl substituted aldehyde is ethylhexaldehyde.

6. A process in accordance with claim 1 wherein the 2-alkyl substituted aldehyde is 2,2-dimethylpropionaldehyde.

* * * * *